United States Patent [19]

Fujita et al.

[11] Patent Number: 4,751,300
[45] Date of Patent: Jun. 14, 1988

[54] PRODUCTION OF DIOXAZINE COMPOUND

[75] Inventors: Taira Fujita; Yutaka Kayane, both of Osaka, Japan

[73] Assignee: Sumitomo Chemical Company, Limited, Osaka, Japan

[21] Appl. No.: 8,790

[22] Filed: Jan. 30, 1987

[30] Foreign Application Priority Data

Feb. 19, 1986 [JP] Japan .................................. 61-36103
Nov. 10, 1986 [JP] Japan ................................. 61-267163

[51] Int. Cl.⁴ ............................................ C09B 19/02
[52] U.S. Cl. ........................................................ 544/74
[58] Field of Search ............................................ 544/74

[56] References Cited

U.S. PATENT DOCUMENTS 4,345,074  8/1982  Hufnagel ............................ 544/74
4,526,963  7/1985  Duer .................................. 544/74

OTHER PUBLICATIONS

PB Report 65657 (10-1945).

*Primary Examiner*—Richard L. Raymond
*Attorney, Agent, or Firm*—Ladas & Parry

[57] ABSTRACT

Dioxazine compound of the formula (I) mentioned below which is useful for dyes or pigments is prepared by heating a compound of

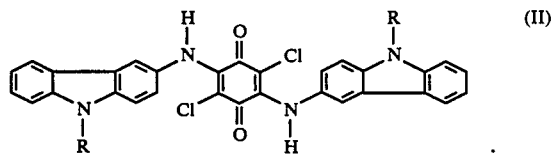

in the presence of inorganic acid with or without an oxidizing agent in an inert organic solvent:

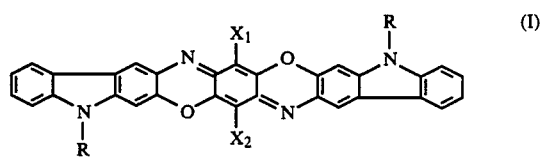

wherein R is defined above; $X_1$ and $X_2$ are selected from a hydrogen atom and a chlorine atom.

14 Claims, No Drawings

PRODUCTION OF DIOXAZINE COMPOUND chlorine atom, is prepared by heating a compound of the formula

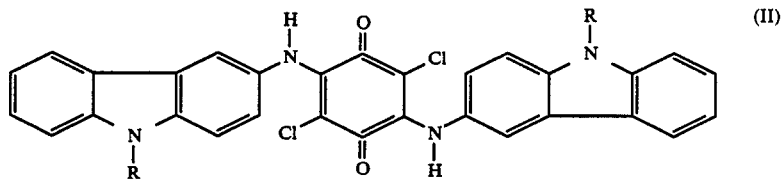

This invention relates to an improvement in production of a dioxazine compound which is useful for dyes, pigments or functional colorants.

There are many processes for preparing a dioxazine compound from a compound of the formula

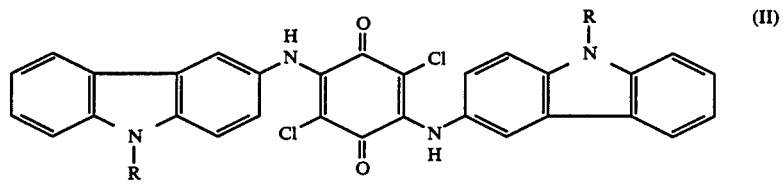

wherein R is an alkyl group having 1–4 carbon atoms. One of the processes is conducted in the presence of benzenesulfonyl chloride (PB Report 65657). Another process is carried out in the presence of organic acid such as p-toluenesulfonic acid. (Japanese Kokai No. 58-84857).

Difficulties encountered in the known processes are that a long period of time is necessary for filtration and isolation of the desired compound and that a large amount of an organic solvent is needed to wash the compound filtered. When the amount of the organic solvent for washing is too short, hue and other properties of a dye or pigment with dioxazine compound obtained are not so stable that after-treatment is hardly effected. An excess of the oxidizing agent or organic acid, e.g., more than one mole thereof per mole of the compound (II) is necessary in order to effect cyclization, in these known processes. The higher yield is, the more the oxidizing agent or the organic acid is necessary. Dioxazine compound produced is usually contaminated with a considerable amount of various reaction products of the oxidizing agent employed or the organic acid left unchanged.

After long study to dissolve difficulties encountered above, i.e., contamination of a dioxazine product with an oxidizing agent and the like, the use of a small amount of inorganic acid such as hydrochloric acid with or without an oxidizing agent in place of the oxidizing agent mentioned above is found to be very effective.

According to the present invention, a dioxazine compound of the formula

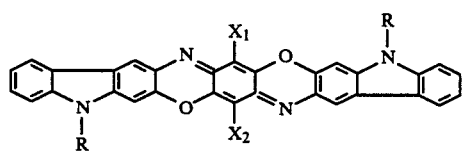

wherein R is an alkyl group having 1–4 carbon atoms; and $X_1$ and $X_2$ are selected from a hydrogen atom and a chlorine atom, is prepared by heating a compound of the formula wherein R is the same as defined above, in an inert organic solvent in the presence of inorganic acid with or without an oxidizing agent.

The inert organic solvent is chlorobenzene, dichlorobenzene, trichlorobenzene or a mixture thereof, nitrobenzene and alkyl benzene or alkyl naphthalene whose boiling point is not lower than 110° C., preferably chlorobenzenes, nitrobenzene and alkylbenzenes.

The inorganic acid includes hydrochloric acid, sulfuric acid, hydrobromic acid and phosphoric acid, preferably hydrochloric acid and sulfuric acid, most preferably hydrochloric acid. The acid is used in a catalytic amount, at the least, but usually at least 0.01 mole, preferably 0.01–1.0 mole per mole of the compound (II).

The oxidizing agent is p-benzoquinone or derivatives thereof, o-benzoquinone or derivatives thereof, benzenesulfonyl chloride or derivatives thereof and esters of benzenesulfonic acid, preferably p-benzoquinone, p-chloranil, tetracyanobenzoquinone, dicyanodichlorobenzoquinone, o-chloranil, p-toluenesulfonyl chloride and benzenesulfonyl chloride. The oxidizing agent is used in an amount of 0.0001–1.0 mole, preferably 0.01–0.5 mole per mole of the compound (II).

Reaction is usually carried out at a temperature of 100° C. or higher, industrially 110°–200° C., preferably 130°–180° C., for 3–12 hours, preferably 4.0–8.0 hours.

After the reaction is over, filtration is effected to obtain crystals which are then washed with an enough solvent. Pressing and then drying gives the dioxazine compound (I) with high yield.

The present process is economical in cost, because amounts of reagents necessary are small. The process is economical, too, from view points of energy conservation and resources saving. Labour and energy necessary for recovery of solvents and for after-treatment of waste materials are greatly lessened, because a period of time for filtration is shortened and an amount of solvents necessary is lowered. Dioxazine compound obtained by the present process is superior in tinting strength, gloss and transparency as pigments.

In the following examples, parts and % are those by weight.

EXAMPLE 1

To o-dichlorobenzene (400 parts) were added 2,5-dichlor-3,6-bis(9-ethyl-3-carbazolylamino)-1,4-benzoquinone (60 parts) and then 36% HCl (1.0 part). The mixture was heated to 155°–160° C. under stirring and was kept at this temperature for five hours. After being cooled to 120° C., the reaction mixture was filtered at this temperature. The precipitate was washed with o-dichlorobenzene (400 parts, 100° C.), methanol (150 parts) and water (300 parts) in this order and was subjected to pressing. The cake produced was dried to obtain dioxazine compound wherein R of the formula (I) is —$C_2H_5$ (51.0 parts).

Elemental analysis: C: 71.0%, H: 4.1%, N: 9.7%, Cl: 9.0%.

The filtration and washing were completed in shorter period of time and an amount of the solvent for washing was smaller than those for the conventional process, respectively.

EXAMPLE 2

To o-dichlorobenzene (400 parts) were added 2,5-dichloro-3,6-bis(9-ethyl-3-carbazolylamino)-1,4-benzoquinone (60 parts) and then 36% HCl (2.5 parts). The mixture was heated up to 165°–170° C. under stirring and was kept at this temperature for five hours. After being cooled to 120° C., the mixture was filtered at this temperature. The precipitate was washed with o-dichlorobenzene (400 parts, 100° C.), methanol (150 parts) and water (300 parts) in this order and was subjected to pressing. The cake was dried to obtain a dioxazine compound in which R of the formula (I) is $C_2H_5$ (50.5 parts).

Elemental analysis: C: 70.5%, H: 4.0%, N: 9.6%, Cl: 10.0%.

The filtration and washing were completed in a shorter period of time and an amount of the solvent for washing was smaller than those for the conventional process, respectively.

EXAMPLE 3

To o-dichlorobenzene (400 parts) were added 2,5-dichloro-3,6-bis(9-ethyl-3-carbazolylamino)-1,4-benzoquinone (60 parts) and then 78% sulfuric a (2.0 parts) and tetracyanobenzoquinone (3.0 parts). The mixture was heated up to 155°–160° C. under stirring and was kept at this temperature for five hours. After being cooled to 120° C., the mixture was filtered at this temperature. The precipitate was washed with o-dichlorobenzene (400 parts, 100° C.), methanol (150 parts) and water (300 parts) in this order and was subjected to pressing. The cake produced was dried to obtain a dioxazine compound wherein R of the formula (I) is $C_2H_5$ (50.0 parts).

Elemental analysis: C: 69.8%, H: 4.1%, N: 9.5%, Cl: 11.3%.

The filtration and washing were completed in a shorter period of time and an amount of the solvent for washing was smaller than those for the conventional process, respectively.

EXAMPLE 4

Example 3 was repeated except that 78% sulfuric acid (6.0 parts) was used in place of 78% sulfuric acid and tetracyanobenzoquinone. The same results were obtained.

EXAMPLE 5

To o-dichlorobenzene (400 parts) were added 2,5-dichloro-3,6-bis(9-ethyl-3-carbazolylamino)-1,4-benzoquinone (60 parts), and then 36% hydrochloric acid (0.5 part). The mixture was heated up to 145°–150° C. under stirring and was kept at this temperature for 12 hours. After being cooled to 120° C., the mixture was filtered at this temperature. The precipitate was washed with o-dichlorobenzene (400 parts, 100° C.), methanol (150 parts) and water (300 parts) in this order and was subjected to pressing. The cake produced was dried to obtain a dioxazine compound wherein R of the formula (I) is $C_2H_5$ (51.0 parts).

Elemental analysis: C: 72.0%, H: 4.1%, N: 9.8%, Cl: 8.5%.

The filtration and washing were very easy and an amount of the solvent for washing was smaller than that required for the conventional process.

EXAMPLE 6

To o-dichlorobenzene (400 parts) were added 2,5-dichloro-3,6-bis(9-ethyl-3-carbazolylamino)-1,4-benzoquinone (60 parts) and then 36% hydrochloric acid (1.0 part) and p-chloranil (4 parts). The mixture was heated up to 165°–170° C. under stirring and was kept at this temperature for five hours. After being cooled to 120° C., the mixture was filtered at this temperature. The precipitate was washed with o-dichlorobenzene (400 parts, 100° C.), methanol (150 parts) and water (300 parts) in this order and was subjected to pressing. The cake was dried to obtain a dioxazine compound wherein R of the formula (I) is $C_2H_5$ (51.5 parts).

Elemental analysis: C: 70.6%, H: 4.1%, N: 9.7%, Cl: 11.4%.

The filtration and washing were very easy and an amount of the solvent for washing was smaller than that required for the conventional process.

EXAMPLE 7

Example 6 was repeated except that 36% hydrochloric acid (1.0 part) was used in place of 36% hydrochloric acid and p-chloranil to obtain the similar dioxadizine compound thereto.

Elemental analysis: C: 70.6%, H: 4.1%, N: 9.7%, Cl: 10.0%.

EXAMPLE 8

To trichlorobenzene (400 parts) were added 2,5-dichloro-3,6-bis(9-ethyl-3-carbazolylamino)-1,4-benzoquinone (60 parts) and then 70% sulfuric acid (1.0 part). The mixture was heated up to 190°–200° C. under stirring and was kept at this temperature for five hours. After being cooled to 120° C., the mixture was filtered at this temperature. The precipitate was washed with trichlorobenzene (400 parts, 100° C.), methanol (150 parts) and water (300 parts) in this order and was subjected to pressing. The cake was dried to obtain a dioxazine compound wherein R of the formula (I) is $C_2H_5$ (49.0 parts).

Elemental analysis: C: 71.0%, H: 4.1%, N: 10.0%, Cl: 8.5%.

The filtration and washing were very easy and an amount of the solvent for washing was smaller than that for the conventional process.

EXAMPLE 9

Example 8 was repeated except that 36% hydrochloric acid (1.0 part) was used in place of 70% sulfuric acid. The same result as above was obtained.

EXAMPLE 10

To o-dichlorobenzene (400 parts) were added 2,5-dichloro-3,6-bis(9-ethyl-3-carbazolylamino)-1,4-benzoquinone (60 parts) and then 70% sulfuric acid (1.0 part) and p-benzensulfonyl chloride (5.0 parts). The mixture was heated up to 165°–170° C. under stirring and was kept at this temperature for five hours. After being cooled to 120° C., the mixture was filtered at this temperature. The precipitate was washed with o-dichlorobenzene (400 parts, 100° C.), methanol (150 parts) and water (300 parts) in this order and was subjected to pressing. The cake was dried to obtain a dioxazine compound wherein R of the formula (I) is $C_2H_5$ (51.0 parts).

Elemental analysis: C: 71.0%, H: 4.1%, N: 9.7%, Cl: 10.8%.

The filtration and washing were completed in a shorter period of time and an amount of the solvent for washing was smaller than those required for the conventional process, respectively.

EXAMPLE 11

To o-dichlorobenzene (400 parts) were added 2,5-dichloro-3,6-bis(9-ethyl-3-carbazolylamino)-1,4-benzoquinone (60 parts) and then 98% sulfuric acid (0.5 part) and o-chloranil (2 parts). The mixture was heated up to 165°–170° C. and was kept at this temperature for five hours. After being cooled to 120° C., the mixture was filtered at this temperature. The precipitate was washed with o-dichlorobenzene (400 parts, 100° C.), methanol (150 parts) and water (300 parts) in this order and was subjected to pressing. The cake was dried to obtain a dioxazine compound wherein R of the formula (I) is $C_2H_5$ (51.0 parts).

Elemental analysis: C: 71.0%, H: 4.1%, N: 9.7%, Cl: 10.5%.

The filtration and washing were able to effect in a shorter period of time and an amount of the solvent for the washing was smaller than those for the conventional process, respectively.

EXAMPLE 12

To nitrobenzene (400 parts) were added 2,5-dichloro-3,6-bis(9-ethyl-3-carbazolylamino)-1,4-benzoquinone (60 parts) and then 36% hydrochloric acid (1 part) and benzoquinone (2.0 parts). The mixture was heated up to 155°–160° C. under stirring and was kept at this temperature for five hours. After being cooled to 120° C., the mixture was filtered at this temperature. The precipitate was washed with o-dichlorobenzene (400 parts, 100° C.), methanol (150 parts) and water (300 parts) in this order and was subjected to pressing. The cake was dried to obtain a dioxazine compound wherein R of the formula (I) is $C_2H_5$ (51.0 parts).

Elemental analysis: C: 71.0%, H: 4.1%, N: 9.5%, Cl: 10.5%.

The filtration and washing were completed in a shorter period of time and an amount of the solvent for washing was smaller than those for the conventional process, respectively.

EXAMPLE 13

To mesitylene (400 parts) were added 2,5-dichloro-3,6-bis(9-ethyl-3-carbazolylamino)-1,4-benzoquinone (60 parts) and then 36% hydrochloric acid (1.0 part). The mixture was heated up to 155°–160° C. under stirring and was kept at this temperature for five hours. After being cooled to 120° C., the mixture was filtered at this temperature. The precipitate was washed with o-dichlorobenzene (400 parts, 100° C.), methanol (150 parts) and water (300 parts) in this order and was subjected to pressing. The cake was dried to obtain a dioxazine compound wherein R of the formula (I) is $C_2H_5$ (51.0 parts).

Elemental analysis: C: 71.0%, H: 4.1%, N: 9.7%, Cl: 9.0%.

The filtration and washing were completed in a shorter period of time and an amount of the solvent for washing was smaller than those for the conventional process, respectively.

COMPARISON EXAMPLE 1

(Conventional Process)

To o-dichlorobenzene (400 parts) was added 2,5-dichloro-3,6-bis(9-ethyl-3-carbazolylamino)-1,4-benzoquinone (60 parts). The mixture was heated up to 115° C. and benzenesulfonyl chloride (19 parts) was added thereto. The mixture was further heated up to 175°–180° C. and was kept at this temperature for six hours. After being cooled to 120° C., the mixture was filtered. The precipitate was washed with o-dichlorobenzene (400 parts, 100° C.) and then with similar o-dichlorobenzene to the former (400 parts), methanol (150 parts) and water (800 parts) in this order, before being subjected to pressing. The cake was dried to obtain a dioxazine compound (47.6 parts).

Elemental analysis: C: 70.0%, H: 3.8%, N: 9.6%, Cl: 11.5%, S: 0.3%.

The filtration and washing with o-dichlorobenzene took a long time (about one hour).

Elemental analysis of a dioxazine compound obtained without the second washing with o-dichlorobenzene, i.e., when the washing with the o-dichlorobenzene (100° C.) was followed by the washing with methanol and with water, gave the following:

C: 70.0%, H: 4.0%, N: 9.0%, Cl: 11.3%, S: 1.5%.

A large amount of S was contained and washing was not sufficient.

COMPARISON EXAMPLE 2

(Conventional Process)

To o-dichlorobenzene (300 parts) were added 2,5-dichloro-3,6-bis(9-ethyl-3-carbazolylamino)-1,4-benzoquinone (60 parts) and then p-toluene sulfonic acid (26 parts). The mixture was kept at 80°–85° C. and then added under stirring to o-dichlorobenzene (100 parts, 175°–180° C.) over three hours. The mixture was kept at 175°–180° C. for six hours after the addition was over. The mixture was cooled to 120° C. and then filtered. The precipitate was washed with o-dichlorobenzene (400 parts, 100° C.) and then the same washing was repeated three times, followed by washing with methanol (150 parts) and then with water (300 parts), before being subjected to pressing. The cake was dried to obtain a dioxazine compound (38.7 parts).

Elemental analysis: C: 66.0%, H: 4.0%, N: 7.8%, Cl: 6.5%, S: 3.3%.

A large amount of S was contained. The filtration and washing with o-dichlorobenzene took a long time (about 2 hours).

REFERENCE EXAMPLE (USE EXAMPLE)

A mixture each containing dioxazine compounds (100 parts each) respectively obtained in examples 1 and 6 and comparison example 1 wherein washing with o-dichlorobenzene was effected two times, table salt (300 mesh size, 700 parts) and ethylene glycol (150 parts) was ground in a kneader having two pestles used for experiment for seven hours holding a temperature at 70°-75° C. Mass each was added to hot water (80° C., 2000 parts) and stirred before filtering. The precipitate each was washed with water (4000 parts) and dried. Nitrocellulose or polyamide gravure ink in which pigment was made from the dried cake above was preprared. Dioxazine compound obtained in the comparison example 1 was taken as standard.

|  | Specific surface *1 | Tinting strength *2 | Gloss *3 | Transparency *4 |
|---|---|---|---|---|
| Example 1 | 93 m²/g | 120% | +2 | +1 to 2 |
| Example 6 | 90 m²/g | 115% | +2 | +1 to 2 |
| Comparison example 1 | 80 m²/g | 100% | Standard | Standard |

Notes
*1 gas adsorption method (BET).
*2 an amount of a sample compound in ink to show the same tinting strength as that of the standard compound which is fixed at 100%.
*3 JIS L 0804, based on discoloration grey scale; difference corresponding to No. 4 color chip is chosen as 2 and difference to Nos. 4-5 as 1.
*4 the similar manner to *3 above.

We claim:

1. A process for preparing a dioxazine compound of the formula

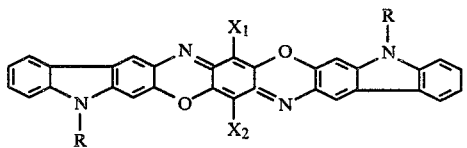

wherein R is an alkyl group of 1-4 carbon atoms; and $X_1$ and $X_2$ are selected from a hydrogen atom and a chlorine atom, which comprises heating a compound having the formula

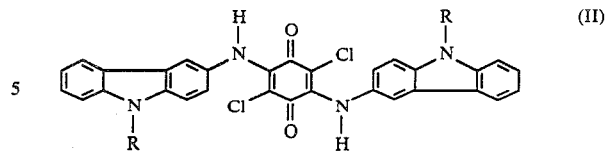

wherein R is the same as defined above, in an inert organic solvent in the presence of at least a catalytic amount of an inorganic acid with or without an oxidizing agent.

2. A process according to claim 1 wherein the inorganic acid is hydrochloric acid.

3. A process according to claim 1 wherein the inorganic acid is sulfuric acid.

4. A process according to claim 1 wherein the oxidizing agent is p-benzoquinone or derivatives thereof.

5. A process according to claim 1 wherein the oxidizing agent is o-benzoquinone or derivatives thereof.

6. A process according to claim 1 wherein the oxidizing agent is benzenesulfonyl chloride or derivatives thereof.

7. A process according to claim 1 wherein the oxidizing agent is ester of benzenesulfonic acid.

8. A process according to claim 1 wherein heating is made at 110°-200° C.

9. A process according to claim 1 wherein the inert organic solvent is chlorobenzene, dichlorobenzene, trichlorobenzene, or a mixture thereof, nitrobenzene or alkyl benzene having the boiling point of not lower than 110° C.

10. A process according to claim 1 wherein the amount of inorganic acid is at least 0.01 mole per mole of the compound (II).

11. A process according to claim 10 wherein the amount of inorganic acid is 0.01-1.0 mole per mole of the compound (II).

12. A process according to claim 1 wherein the oxidizing agent is 0.0001-1.0 mole per mole of the compound (II).

13. A process according to claim 12 wherein the oxidizing agent is 0.01-0.5 mole per mole of the compound (II).

14. A process, as in claim 1 wherein the inorganic acid is selected from the group consisting of hydrochloric, sulfuric, hydrobromic and phosphoric acids.

* * * * *